United States Patent [19]

Klausener et al.

[11] Patent Number: 4,784,997
[45] Date of Patent: Nov. 15, 1988

[54] 1-H-PYRIDO-[3,2-B][1,4]-THIAZINE

[75] Inventors: Alexander Klausener; Gerd Fengler; Hans-Josef Buysch, all of Krefeld; Bernhard Pelster, St. Augustin, all of Fed. Rep. of Germany

[73] Assignee: Bayer Aktiengesellschaft, Leverkusen, Fed. Rep. of Germany

[21] Appl. No.: 942,468

[22] Filed: Dec. 16, 1986

[30] Foreign Application Priority Data

Dec. 19, 1985 [DE] Fed. Rep. of Germany ....... 3545097

[51] Int. Cl.⁴ .................... A61K 31/54; C07D 513/04; C07D 513/12
[52] U.S. Cl. .......................................... 224/2; 544/48; 544/34
[58] Field of Search ....................... 544/51, 52, 34, 48; 514/224, 225, 222

[56] References Cited

U.S. PATENT DOCUMENTS 3,299,057 1/1967 Gross et al. ............................ 544/34
3,546,220 12/1970 Stein et al. ............................ 544/48
3,767,653 10/1973 Krapcho ................................ 544/52
3,855,214 12/1974 Roderick ............................... 544/48

FOREIGN PATENT DOCUMENTS 0100527 2/1984 European Pat. Off. .
0101898 3/1984 European Pat. Off. .

Primary Examiner—John M. Ford
Attorney, Agent, or Firm—Sprung Horn Kramer & Woods

[57] ABSTRACT

1-H-pyrido-[3,2-b][1,4]-thiazines of the formula

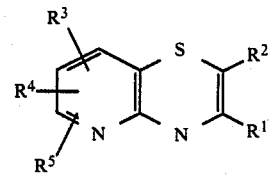

are prepared by the reaction of 2-halogenocarbonyl compounds an 2-amino-3-pyridinethiols. These compounds are useful as medicaments especially as inhibitors of lipoxygenase.

7 Claims, No Drawings

1-H-PYRIDO-[3,2-B][1,4]-THIAZINE

The present invention relates to new 1-H-pyrido-[3,2-b][1,4]-thiazines and their salts, to a process for their preparation and to their use in medicaments.

It is known that the metabolites of arachidonic acid formed by the enzyme lipoxygenase are involved in the development of inflammatory and allergic processes [Goetzl, Immunology 40 709 (1980); Ford-Hutchinson, J. Pharm. Pharmacol. 32 517 (1980) and Nature 286 264 (1980; Samuelsson, Trends in Pharmacol. Sci. May 1980 227; Borgeat, J. Med. Chem. 24 121 (1981)].

New 1-H-pyrido-[3,2-b][1,4]-thiazines of the formula

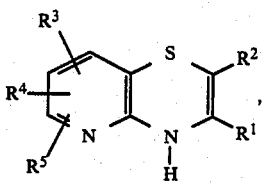

(I)

in which $R^1$ denotes hydrogen, optionally substituted alkyl or alkenyl or the group

in which $R^6$ represents optionally substituted alkyl, aryl or alkoxy, $R^2$ denotes hydrogen, nitrile, the group

in which $R_7$ represents optionally substituted alkyl or aryl, or the group

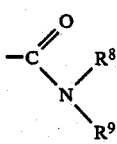

in which $R^8$ and $R^9$ are identical or different and represent hydrogen, optionally substituted alkyl or aryl, and it being possible for the radicals to be linked by a hydrocarbon bridge, which can also optionally be interrupted by further heteroatoms, to form a 5- or 6-membered, optionally substituted heterocycle, or the group

in which $R^{10}$ represents optionally substituted alkyl, it being possible for $R^1$ and $R^{10}$ to form an optionally substituted 5- to 8-membered carbocycle, or optionally substituted aryl, and $R^3$, $R^4$ and $R^5$ are identical or different and denote hydrogen, halogen, optionally substituted alkyl, alkoxy, aryloxy, alkylthio, arylthio or the group

in which $R^{11}$ and $R^{12}$ are identical or different and represent hydrogen, optionally substituted alkyl or aryl, and it being possible for the radicals to be linked by a hydrocarbon bridge, which can optionally also be interrupted by further heteroatoms, to form a 5- or 6-membered, optionally substituted heterocycle, and their salts, have been found.

Surprisingly, the new 1-H-pyrido-[3,2-b[]1,4]-thiazines are potent inhibitors of lipoxygenase. Surprisingly, they inhibit lipoxygenase very specifically even at concentrations at which cyclooxygenase is unaffected. This very potent and specific action of the 1-H-pyrido-[3,2-b[]1,4]-thiazines could not have been expected.

In general, alkyl represents straight-chain or branched hydrocarbon radicals having 1 to 8 carbon atoms. Lower alkyl having 1 to 6 carbon atoms is preferred. Examples which may be mentioned are methyl, ethyl, propyl, isopropyl, butyl, isobutyl, pentyl, isopentyl, hexyl and isohexyl.

In general, alkenyl represents an unsaturated straight-chain or branched hydrocarbon radical having 1 to 8 carbon atoms and one or two, preferably one, dlouble bond. Lower alkenyl having 2 to, say, 6 carbon atoms is preferred. Vinyl may be mentioned as an example.

In general the alkyl in the alkoxycarbonyl, acid amide and alkylcarbonyl radicals has the abovementioned range of meanings.

Examples of alkoxycarbonyl which may be mentioned are: methoxycarbonyl, ethoxycarbonyl, isopropoxycarbonyl and isopentoxycarbonyl.

Examples of acid amide radicals which may be mentioned are: methylamide, t-butylamide, morpholinide and p-methoxyanilide.

Examples of alkylcarbonyl radicals which may be mentioned are:
methylcarbonyl, butylcarbonyl, isopentylcarbonyl and isohexylcarbonyl.

In the case where $R^1$ and $R^{10}$ are linked to form a 5- to 8-membered, optionally substituted carbocycle, a linking member which may be mentioned is a hydrocarbon chain which contains 2 to 5 carbon atoms and is optionally substituted by lower alkyl. Examples of carbocycles which have been formed in this way and may be mentioned are: cyclo-pent-2-en-1-one, cyclo-hex-2-en-1one and 5,5-dimethyl-cyclo-hex-2-en-1-one.

In general, aryl represents an aromatic radical having 6 to, say, 12 carbon atoms. Preferred aryl radicals are phenyl, naphthyl and biphenyl, preferably phenyl.

In general, alkoxy represents a straight-chain or branched hydrocarbon radical which has 1 to 8 carbon atoms and is bonded via an oxygen atom. Lower alkoxy having 1 to, say, 6 carbon atoms is preferred. Examples which may be mentioned are methoxy, ethoxy, propoxy, isopropoxy, butoxy, isobutoxy, pentoxy, isopentoxy, hexoxy and isohexoxy.

In general, aryloxy represents an aryl radical which has 6 to 12 carbon atoms and is bonded via oxygen. Phenyloxy is preferred.

In general, alkylthio represents a straight-chain or branched hydrocarbon radical which has 1 to 8 carbon atoms and is bonded via a sulphur atom. Lower alkylthio having 1 to, say, 6 carbon atoms is preferred. Examples which may be mentioned are ethylthio, butylthio, tert.-butylthio and hexylthio.

In general, arylthio represents an aryl radical which has 6 to 12 carbon atoms and is bonded via a sulphur atom. [m-(Trifluoromethyl)phenyl]thio, [p-(fluoro)-phenyl]thio, and [p-(t-butyl)phenyl]thio may be mentioned as preferred.

The radicals $R^8$ and $R^9$ and $R^{11}$ and $R^{12}$ can be linked by a hydrocarbon bridge, which can optionally also be interrupted by further heteroatoms, to form a 5- or 6-membered, optionally substituted heterocycle. Heteroatoms which may be mentioned are one or two oxygen and/or nitrogen and/or sulphur atoms. Pyrrolyl, pyrimidyl, imidazolyl, morpholinyl and N-methylpiperazinyl may be mentioned here as preferred.

In general, halogen denotes fluorine, chlorine, bromine and iodine, preferably fluorine, chlorine and bromine.

The said radicals can optionally be substituted. Examples of substituents which may be mentioned are halogen, preferably fluorine, chlorine and bromine, nitro, cyano, methoxycarbonyl, ethoxycarbonyl, and trifluoromethyl.

The 1-H-pyrido-[3,2-b][1,4]-thiazines according to the invention can also be in the form of their salts. In general, salts with organic or inorganic acids may be mentioned here.

Physiologically acceptable salts are preferred within the scope of the present invention. Physiologically acceptable salts of the 1-H-pyrido-[3,2-b][1,4]-thiazines are preferably salts with inorganic acids such as, for example, hydrochlorides, hydrobromides, sulphates, nitrates, hydrogen sulphates, phosphates or hydrogen phosphates, or with organic acids such as, for example, formates, acetates, benzoates, maleates, fumarates, tartrates or lactates.

Preferred 1-H-pyrido-[3,2-b][1,4]-thiazines of the formula (I) are those
in which
$R^1$ denotes hydrogen, optionally substituted alkyl ($C_1$ to $C_8$) or alkenyl ($C_2$ to $C_8$), or the group

in which $R^6$ represents optionally substituted alkyl ($C_1$ to $C_8$), alkoxy ($C_1$ to $C_8$) or aryl ($C_6$ to $C_{12}$),
$R^2$ denotes hydrogen, nitrile, the group

in which $R^7$ represents optionally substituted alkyl ($C_1$ to $C_8$), or the group

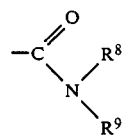

in which
$R^8$ and $R^9$ are identical or different and represent hydrogen, optionally substituted alkyl ($C_1$ to $C_8$) or aryl ($C_6$ to $C_{12}$), and it being possible for the radicals to be linked by a hydrocarbon bridge, which can optionally be interrupted by one or two oxygen and/or nitrogen and/or sulphur atoms, to form a 5- or 6-membered, optionally substituted heterocycle, or the group

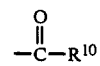

in which $R^{10}$ represents optionally substituted alkyl ($C_1$ to $C_8$), it being possible for $R^1$ and $R^{10}$ to form an optionally substituted 5- to 8-membered carbocycle, or optionally substituted aryl ($C_6$ to $C_{12}$),
$R^3$ denotes hydrogen, and
$R^4$ and $R^5$ are identical or different and denotes hydrogen, halogen, optionally substituted alkyl ($C_1$ to $C_8$), alkoxy ($C_1$ to $C_8$), aryloxy ($C_6$ to $C_{12}$), alkylthio ($C_1$ to $C_8$), arylthio ($C_6$ to $C_{12}$) or the group

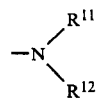

in which
$R^{11}$ and $R^{12}$ are identical or different and represent hydrogen, optionally substituted alkyl ($C_1$ to $C_8$) or aryl ($C_6$ to $C_{12}$), and it being possible for the radicals to be linked by a hydrocarbon bridge, which can optionally be interrupted by one or two oxygen and/or nitrogen and/or sulphur atoms, to form a 5- or 6-membered, optionally substituted heterocycle, and their salts.

Particularly preferred 1-H-pyrido-[3,2-b][1,4]-thiazines of the formula (I) are those in which
$R^1$ denotes hydrogen, lower alkyl which is optionally substituted by carboxymethyl or carboxyethyl, or vinyl or methoxycarbonyl, ethoxycarbonyl
$R^2$ denotes hydrogen, methoxycarbonyl, ethoxycarbonyl or the group

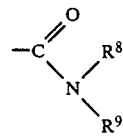

in which
$R^8$ and $R^9$ are identical or different and represent hydrogen, lower alkyl or phenyl and it being possible for the radicals to be linked to form a piperidyl, morpholinyl, piperazinyl or N-methylpiperazinyl radical, or the group

in which
R[10] denotes methyl or ethyl, and it being possible for R[1] and R[10] to form a 5- to 8-membered carbocycle which is optionally substituted by one or two methyl groups, R[3] and R[4] denote hydrogen, lower alkyl or halogen, and R[5] denotes hydrogen, fluorine, chdlorine, bromine, lower alkyl, lower alkoxy, piperidyl, morpholinyl or N-methylpiperazinyl, and their salts.

The following 1-H-pyrido-[3,2-b][1,4]-thiazines may be mentioned as examples:

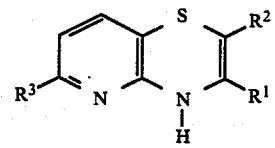

| R[1] | R[2] | R[3] |
|---|---|---|
| H | COOMe | Et |
| H | COOBu | Me |
| H | COOBu[t] | H |
| Me | COOMe | Et |
| Me | COOBu | Me |
| Me | COOBu[t] | H |
| Bu[t] | COOMe | Et |
| Bu[t] | COOBu | Me |
| Bu[t] | COOBu[t] | H |
| Me | COOEt | F |
| Me | COOPr[i] | Cl |
| Me | COOBu[t] | Br |
| H | CONH2 | OEt |
| Me | CONHMe | O(p-Cl—Ph) |
| Et | CONHBu | O(o-CN—Ph) |
| Pr | CONPh | O(m-NO2—Ph) |
| Pr[i] | CONHCH2CH2OH | SBu |
| Bu | CONHCH2CH2OMe | S(p-Cl—Ph) |
| Bu[i] | CONCH2CH2NH2 | S(o-OMe—Ph) |
| Bu[t] | CONCH2CH2NHEt | S(m-NO2—Ph) |
| H | CONHCH2CH2NMe2 | NMe2 |
| Me | CONMe2 | NEt2 |
| Et | CONMeEt | NMePh |
| Me | CN | Me |
| COOEt | COOEt | Me |
| COOBu | COOBu | Me |
| COOEt | H | H |
| CH2COOEt | H | H |
| CH2COOBu[t] | H | H |
| Me | COOEt | N(CH2CH2OMe)2 |
| Me | COOEt | N(CH2CH2NMe2)2 |
| Et | COOCH2CHF2 | NEt(p-F—Ph) |
| Me | COOCH2CH2Cl | NMe(m-NO2—Ph) |
| H | COOCH2CN(Me)OMe | NMe(p-Me—Ph) |
| Bu[t] | COOCH2CH2CH2OMe | NMe(p-Cl—Ph) |
| CH=CH2 | H | H |
| H | Ph | H |
| H | p-Cl—Ph | H |
| H | p-OMe—Ph | H |
| H | m-CN—Ph | Me |
| H | m-NO2—Ph | Cl |
| H | o-Br—Ph | Br |
| H | o-F—Ph | F |
| H | CO—Me | H |
| H | CO—Et | OEt |
| Me | 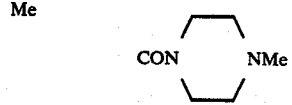 | Cl |
| Me |  | F |

-continued

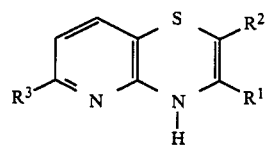

| R¹ | R² | R³ |
|---|---|---|
| Me |  CON⟨ring⟩ | OEt |
| Me | 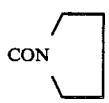 CON⟨ring⟩ | SPh |
| H | COOBu | 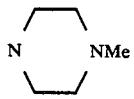 N⟨ ⟩NMe |
| H | COOBu |  N⟨ ⟩O |
| H | CONEt₂ |  N⟨piperidinyl⟩ |
| H | CONEt₂ | 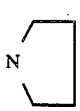 N⟨pyrrolidinyl⟩ |

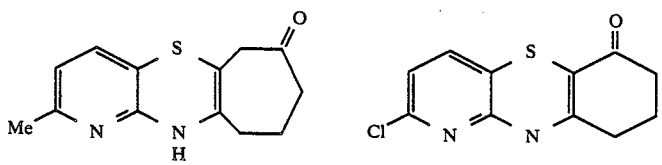

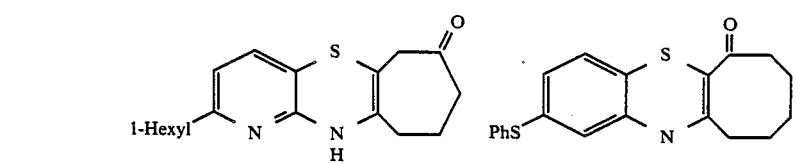

A process for the preparation of 1-H-pyrido-[3,2-b][1,4]-thiazines has also been found, which is characterized in that 2-amino-3-pyridinethiols of the formula

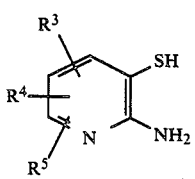 (II)

in which

R³, R⁴ and R⁵ are identical or different and denote hydrogen, halogen, optionally substituted alkyl, alkoxy, aryloxy, alkylthio, arylthio, or the group

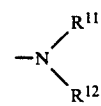

in which

R¹¹ and R¹² are identical or different and denote hydrogen, optionally substituted alkyl or aryl, and it being possible for the radicals to be linked by a hydrocarbon bridge, which can optionally also be interrupted by further heteroatoms, to form a 5- or 6-membered, optionally substituted heterocycle, are reacted in the presence of a base with an α-halogenocarbonyl compound of the formula

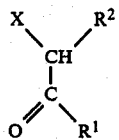 (III)

in which
X denotes halogen,
R¹ denotes hydrogen, optionally substituted alkyl or alkenyl or the group

in which R⁶ represents optionally substituted alkyl, alkoxy or aryl, and
R² denotes hydrogen, nitrile, the group

in which R⁷ represents optionally substituted alkyl or aryl, or the group

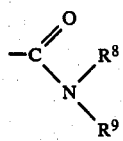

in which
R⁸ and R⁹ are identical or different and represent hydrogen, optionally substituted alkyl or aryl, and it being possible for the radicals to be linked by a hydrocarbon bridge, which can optionally also be interrupted by further heteroatoms, to form a 5- or 6-membered, optionally substituted heterocycle, or the group

in which R¹⁰ represents optionally substituted alkyl, it being possible for R¹ and R¹⁰ to form an optionally substituted 5- to 8-membered carbocycle, or optionally substituted aryl.

The process according to the invention can be illustrated by the following equation

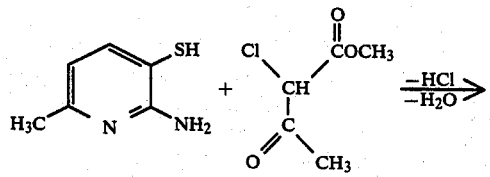

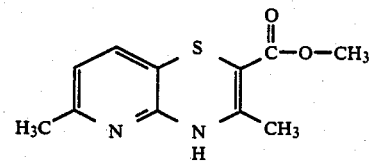

2-Amino-3-pyridinethiols for the process according to the invention can be prepared from acylated 2-aminopyridines and, for example, dibenzyl disulphide. It is unnecessary to use the 2-amino-3-pyridinethiols in purified form for the process according to the invention. They can also be used in the form of their salts, in particular their alkali metal, alkaline earth metal or ammonium salts. It is particularly advantageous to use these thiolates in the crude form resulting from their preparation.

α-Halogenocarbonyl compounds for the process according to the invention are known per se (J. Heterocycl. Chem. 10, 938 (1973); Org. Syntheses 21, 4 (1941); Ann. Chem. 439, 211 (1924)) and can be prepared by, for example, reaction of carbonyl compounds with sulphuryl chloride. α-Halogenocarbonyl compounds which may be mentioned are the fluorine, chlorine, bromine or iodine compounds, preferably the chlorine compounds.

The process according to the invention is carried out in the presence of a base. Suitable for this purpose are inorganic bases such as alkali metal or alkaline earth metal hydroxides and carbonates, and corresponding ammonium compounds, as well as organic bases such as tertiary amines (trialkyl($C_1$-$C_6$)amines) heterocycles (for example pyridine, morpholine and quinoline).

The process according to the invention is preferably carried out in the presence of a diluent. The diluents which can be used are all inert solvents which are not changed under the reaction conditions. These include, preferably, ethers such as dioxane and tetrahydrofuran, dipolar aprotic solvents such as dimethyl sulphoxide, dimethylformamide and N-methylpyrrolidone, water and, especially preferably, lower alcohols such as ethanol, methanol, n- and i-propanol and n-, i- and t-butanol.

The process according to the invention can be carried out in the presence of exclusively one or more organic solvents, in a mixture of such solvents with water, or in one or more solvents which are immiscible with water.

The process according to the invention is generally carried out in the temperature range from about −10° C. to about +100° C., preferably in the temperature range from 0° C. to 60° C.

The process according to the invention can be carried out under atmospheric pressure but also under elevated or reduced pressure (for example in the range from 0.5 to 10.0 bar). It is preferably carried out under atmospheric pressure.

It may prove advantageous to carry out the entire reaction or individual phases of the reaction with exclusion of atmospheric oxygen. This preferably takes place by working under nitrogen or argon.

The process according to the invention can be carried out as follows, for example: the 2-amino-3-pyridinethiols and the α-halogenocarbonyl compounds are reacted in the presence of a base in the molar ratio of about 1:1. It may prove advantageous in individual cases to use excesses of one or other of the components.

After the reaction of the 2-amino-3-pyridinethiols with the α-halogenocarbonyl compounds which has been carried out in the presence of the base, the reaction mixture is neutralized, or the reaction mixture is acidified. It is preferable to use for this purpose inorganic acids, for example hydrochloric acid, sulphuric acid or nitric acid, as well as organic acids, such as acetic acid, or suitable acid ion exchangers.

The said acids can be used alone or in a mixture with other acids, as well as in the pure or in diluted form. Suitable diluents are all inert organic or inorganic solvents.

The reaction mixture is worked up in a manner known per se for the isolation of the 1-H-pyrido-[3,2-b][1,4]-thiazines according to the invention. The reaction products are purified by recrystallization or by use of chromatographic processes (low- medium- and high-pressure liquid chromatography).

A particular embodiment of the process according to the invention for the preparation of 1-H-pyrido-[3,2-b][1,49 -thiazines is characterized in that first 2-pyridineamines of the formula

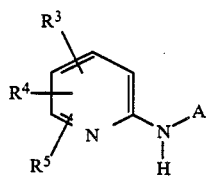

(IV)

in which

A represents an acyl radical of the formula

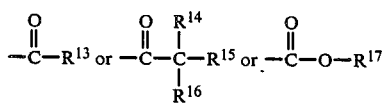

$R^{13}$ representing optionally substituted phenyl, and
$R^{14}$ to $R^{17}$ being identical or different and representing lower alkyl or optionally substituted phenyl and
$R^3$, $R^4$ and $R^5$ are identical or different and denote hydrogen, halogen, optionally substituted alkyl, alkoxy, aryloxy, alkylthio, arylthio or the group

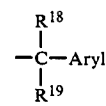

in which
$R^{11}$ and $R^{12}$ are identical or different and denote hydrogen, optionally substituted alkyl or aryl, and it being possible for the radicals to be linked by a hydrocarbon bridge, which can optionally be interrupted by further heteroatoms, to form a 5- or 6-membered, optionally substituted heterocycle are reacted in the presence of organometallic compounds with disulphides of the formula

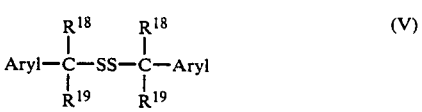

(V)

in which
the radical formula $$-\underset{R^{19}}{\overset{R^{18}}{\underset{|}{C}}}-Aryl$$

represents a thiol protective group, in which
$R^{18}$ and $R^{19}$ are identical or different and denote hydrogen, lower alkyl or aryl, and then either (a) first the thiol protective group is eliminated in the presence of alkali metal and ammonia and/or amine and then the acyl radical is hydrolysed, or (b) first the acyl radical and then the thiol protective group is eliminated in the presence of alkali metal and ammonia and/or amine, and then the resulting 2-amino-3-pyridinethiols are reacted with the α-halogenocarbonyl compound in the presence of a base.

The preparation according to the invention of the 2-amino-3-pyridinethiols can be illustrated by the diagram below:

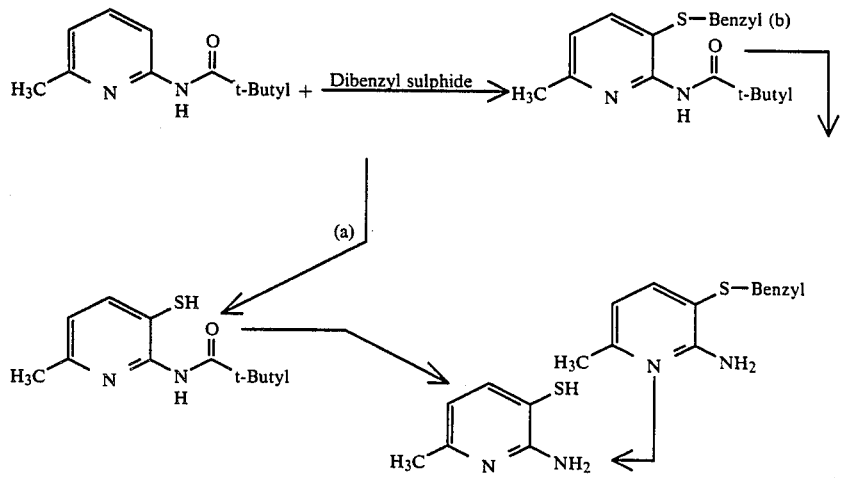

The acylated aminopyridines for the process according to the invention are known per se (J. Org. Chem. 48, 3401 (1983)) and can be prepared by, for example, acylation of the corresponding pyridinamine.

As acyl radicals may be radicals of the formulae

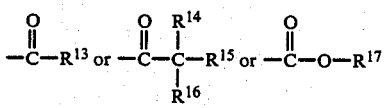

R[13] representing optionally substituted phenyl,
R[14] to R[17] being identical or different and representing lower alkyl or optionally substituted phenyl, may be mentioned Phenyl can be substituted by, for example, methyl, ethyl, propyl or isopropyl.

The following acylated pyridinamines may be mentioned as examples:

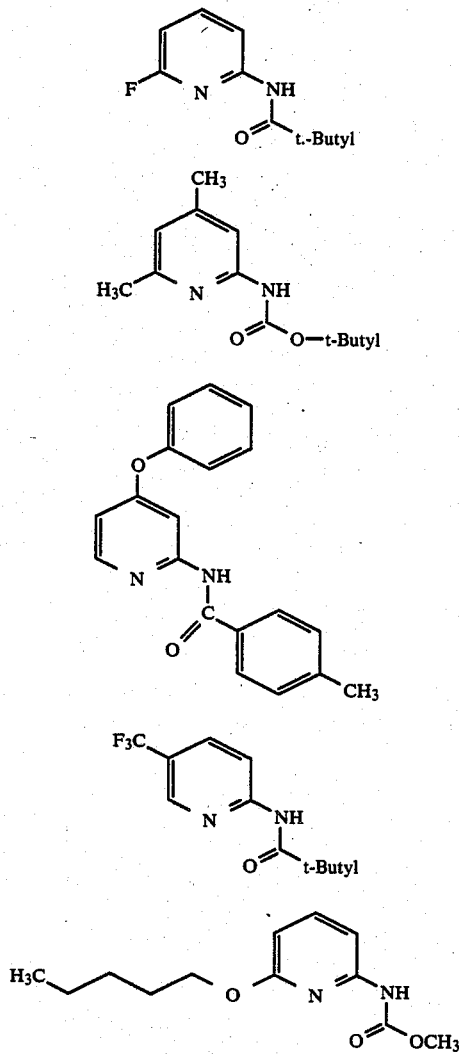

Disulphides for the process according to the invention are known per se (Houben-Weyl, vol. IX, 1955) and can be prepared by, for example, reaction of mercaptans with iodine.

In the disulphides for the process according to the invention, in general aryl represents a radical having 6 to 12 carbon atoms, preferably an optionally substituted (methyl, ethyl, propyl or isopropyl and methoxy, ethoxy, propoxy or isopropoxy) phenyl radical. Phenyl is particularly preferred.

In general lower alkyl represents a straight-chain or branched hydrocarbon radical having 1 to, say, 6 carbon atoms.

The following disulphides may be mentioned as examples: dibenzyl disulphide, di-(p-methoxy-benzyl) disulphide, di-(p-tolyl) disulphide, di-benzhydryl disulphide and bis-(α,α-dimethyl-benzyl) disulphide.

Organometallic compounds are essentially alkyl $(C_1-C_6)$ and/or aryl$(C_6-C_{12})$-lithium compounds. Preferred organometallic compounds are n-, tert.-butyl- and phenyllithium.

Solvents which may be mentioned for this process stage are solvents inert to organolithium. Preferred solvents are ethers such as diethyl ether, 1,2-dimethoxyethane and tetrahydrofuran. Tetrahydrofuran is the preferred solvent.

The process according to the invention can be carried out in the presence of one or more solvents inert to organometallic compounds.

The reaction of the acylated aminopyridines with the disulphides by the process according to the invention can be carried out in the temperature range from $-100°$ C. to $+50°$ C., preferably in the temperature range from $-80°$ C. to $+25°$ C.

It is expedient to carry it out with exclusion of oxygen and moisture. For this reason, the process according to the invention is preferably carried out using dried protective gases such as nitrogen, helium or argon.

In general, the process according to the invention is carried out under atmospheric pressure. However, it is also possible to carry out the process under reduced or elevated pressure (for example in the pressure range 0.5 to 10.0 bar).

The first process stage of the particular embodiment of the process according to the invention is generally carried out as follows:

In general, 2-3 equivalents of the organometallic compound and 1-3 equivalents of the disulphide are used per equivalent of the acylated 2-pyridinamine. This entails both the organometallic compounds and the disulphide being introduced preferably in dissolved form into the reaction mixture.

The solvents preferably used for the disulphide are inert ethers such as diethyl ether, 1,2-dimethoxyethane and, particularly preferably, tetrahydrofuran.

It is also possible and, in certain circumstances, advantageous to add the disulphide in solid form and in excesses greater than mentioned above.

Suitable solvents for the organometallic compounds are inert solvents, preferably hydrocarbons, particularly preferably n-hexane and n-pentane.

The product of the first reaction stage can be isolated by customary methods. However, it is also possible directly to process the reaction product further.

The second stage of the particular embodiment of the process according to the invention can be carried out in two variants.

In variant (a), first the thiol protective group is eliminated in the presence of alkali metal and ammonia and/or amines in anhydrous medium, and then the acyl radical is hydrolyzed.

In variant (b), first the acyl radical is removed, and then the thiol protective group is eliminated in the presence of alkali metals and ammonia and/or amines.

For the elimination of the thiol protective group in variant (a), generally alkali metal such as lithium, sodium or potassium, preferably sodium, is used. Preferably about 2-8 equivalents of the metal, in particularly preferably about 4 equivalents, are made to react per equivalent of the starting material.

In general, amines, preferably primary and/or secondary alkyl($C_1$-$C_6$)amines or liquid ammonia are used for the reaction. The reaction is particularly preferably carried out in liquid ammonia.

However, it is also possible to use mixtures of solvents, for example liquefied ammonia and amines.

In general, the reaction temperature is in the range from $-100°$ to $+50°$ C., preferably in the range from $-80°$ to $+20°$ C. It is advantageous to work with exclusion of oxygen and moisture.

The process according to the invention can be carried out under atmospheric pressure; however, it is also possible to carry out the process under reduced or elevated pressure (for example in the pressure range from 0.5 to 10.0 bar).

After the reaction is complete, the reaction can be stopped by addition of solid ammonium salts (for example ammonium chloride), and subsequent removal of the solvent. The solvent is preferably removed by evaporation under normal pressure or under reduced pressure.

For the elimination of the acyl radical, the residue is treated with an aqueous alkali metal hydroxide solution, preferably with 5-15% strength aqueous sodium or potassium hydroxide solution. It may be advantageous to add suitable organic solvents to the reaction mixture to promote dissolution, preferably lower alcohols or amines, particularly preferably methanol or ethanol.

The temperature of the hydrolysis is generally in the range from 0° to 200° C., preferably in the range from 60° to 100° C.

It may also be advantageous here to work with exclusion of oxygen.

The hydrolysis is generally carried out under atmospheric pressure; however, it is also possible to carry out the hydrolysis under reduced or elevated pressure (for example in the pressure range of 0.5 to 10.0 bar).

It may be advantageous to add reducing organic or inorganic substances during the elimination of the acyl radical, preferably suitable inorganic reducing salts, particularly preferably sodium dithionite, in order to prevent oxidation of the thiols to disulphides.

The substituted 2-amino-3-pyridinethiols are isolated in a manner known per se.

The elimination of the acyl groups in variant (b) can be carried out by treatment with hydrazine. For this purpose, the reaction product of the first stage is reacted with hydrazine or, preferably, with hydrazine hydrate.

It is also possible within the scope of the process according to the invention to carry out the hydrazinolysis with the addition of water and suitable organic solvents and diluents such as alcohols or dioxane. It is also possible to use mixtures of various solvents for this.

In general, the temperature for the hydrazinolysis reaction is in the range from 40° to 200° C., preferably in the range from 60° to 140° C.

The hydrazinolysis is generally carried out under atmospheric pressure; however, it can also be carried out under reduced or elevated pressure (for example in the pressure range from 0.5 to 10.0 bar).

Alternatively, the acyl group can also be eliminated in the presence of alkali (preferably sodium or potassium hydroxide). This entails the reaction product of the first stage being reacted with an aqueous alkali metal hydroxide solution, preferably with 10 to 30% by weight aqueous sodium or potassium hydroxide solution. It may be advantageous to add suitable organic solvents, preferably lower alcohols ($C_1$ to $C_6$), particularly preferably methanol or ethanol, to the reaction mixture to promote dissolution.

The reaction temperature for basic hydrolysis is generally in the range from 25° to 100° C., preferably in the range from 60° to 90° C.

The basic hydrolysis is generally carried out under atmospheric pressure; however, it can also be carried out under reduced or elevated pressure (for example in the pressure range from 0.5 to 10.0 bar).

Another possibility for the elimination of the acyl group is the acid hydrolysis process. This entails the reaction product of the first reaction stage being heated with aqueous mineral acids. Examples suitable for this purpose are sulphuric acid, nitric acid, hydrobromic acid and, preferably, hydrochloric acid. It may be advantageous to add suitable organic solvents, for example lower alcohols ($C_1$ to $C_6$), preferably methanol or ethanol, to the reaction mixture.

The reaction temperature for the acid hydrolysis is in the range from 25° to 200° C., preferably in the range from 60° to 100° C.

The acid hydrolysis is generally carried out under atmospheric pressure, but it can also be carried out under reduced or elevated pressure (for example in the pressure range from 0.5 to 10.0 bar).

Alkali metals, such as lithium, sodium and potassium are preferably used for demasking the thiol group by elimination of the protective group, and sodium is particularly preferably used for demasking the thiol group.

In general, 2-8 equivalents, preferably 3-6 equivalents, of the alkali metal are used per equivalent of the hydrolysis reaction product.

The elimination is generally carried out in the presence of amines, such as primary and/or secondary alkyl ($C_1$-$C_6$)amines or liquid ammonia. The hydrolysis is particularly preferably carried out in liquid ammonia.

However, it is also possible to use mixtures of liquid ammonia and other suitable solvents, such as the said amines.

The elimination of the thiol protective group is generally carried out in the temperature range from $-100°$ to $+50°$ C., preferably in the temperature range from $-80°$ to $+25°$ C. It is advantageous to carry it out with exclusion of atmospheric oxygen and moisture.

The elimination of the thiol protective group is generally carried out under atmospheric pressure; however, it is also possible to carry out this reaction under elevated or reduced pressure (for example in the pressure range from 0.5 to 10.0 bar).

After the reaction is complete, the reaction can be stopped by addition of ammonium salts, for example ammonium chloride, and subsequent removal of the solvent, preferably by evaporation off under atmospheric pressure or reduced pressure.

The 2-amino-3-pyridinethiols are isolated in a manner known per se.

The substituted 2-amino-3-pyridinethiols which are obtained can also be used without previous isolation and purification for the preparation of the 1-H-pyrido-[3,2-b][1,4]-thiazines according to the invention.

The 1-H-pyrido-[3,2-b][1,4]-thiazines according to the invention are active compounds for medicaments and are suitable for therapeutic treatment of humans and animals. They are inhibitors of lipoxygenase and are particularly suitable for the treatment of inflammatory, allergic and asthmatic diseases. They can be used, in particular, as antiinflammatory, antirheumatic, antiarteriosclerotic, antiasthmatic, antiallergic, antimetastatic and gastroprotective agents.

The new active compounds can be converted in a known manner into the customary formulations, such as tablets, capsules, coated tablets, pills, granules, aerosols, syrups, emulsions, suspensions and solutions, using inert, non-toxic, pharmaceutically suitable vehicles or solvents. The therapeutically active compound should in each case be present in a concentration of about 0.5 to 90% by weight of the total mixture, that is to say in amounts which suffice to achieve the dosage range indicated.

The formulations are prepared, for example, by extending the active compounds with solvents and/or vehicles, optionally with the use of emulsifiers and/or dispersing agents, and, for example, when using water as a diluent, organic solvents can optionally be used as auxiliary solvents.

Examples of auxiliaries which may be mentioned are: water, non-toxic organic solvents, such as paraffins (for example petroleum fractions), vegetable oils (for example groundnut oil/sesame oil), alcohols (for example ethyl alcohol and glycerol) and glycols (for example propylene glycol and polyethylene glycol), solid vehicles, such as, for example, natural rock powders (for example koalins, aluminas, talc and chalk), synthetic rock powders (for example highly disperse silica and silicates) and sugars (for example sucrose, lactose and glucose), emulsifiers such as non-ionic anionic emulsifiers (for example polyoxyethylene fatty acid esters, polyoxyethylene fatty alcohol ethers, alkyl-sulphonates and arylsulphonates), dispersing agents (for example lignin, sulphite waste liquors, methylcellulose, starch and polyvinylpyrrolidone) and lubricants (for example magnesium stearate, talc, stearic acid and sodium lauryl sulphate).

Administration is effected in the customary manner, preferably orally or parenterally, in particular perlingually or intravenously. In the case of oral administration, the tablets can, of course, also contain, in addition to the vehicles mentioned, additives such as sodium citrate, calcium carbonate and dicalcium phosphate, together with various additional substances, such as starch, preferably potato starch, gelatine and the like. Furthermore, lubricants such as magnesium stearate, sodium lauryl sulphate and talc can also be used when making tablets. In the case of aqueous suspensions and/or elixirs which are intended for oral use, the active compounds can be mixed with various flavour-improving agents or colorants in addition to the abovementioned auxiliaries.

In the case of parenteral administration, solutions of the active compounds, employing suitable liquid vehicles, can be used.

In general, it has proved advantageous, in the case of intravenous administration, to administer amounts of about 0.01 to 10 mg/kg, preferably about 0.05 to 5 mg/kg, body weight per day to achieve effective results, and in the case of oral administration, the dosage is about 0.05 to 10 mg/kg, preferably 0.1 to 10 mg/kg, of body weight per day.

Nevertheless, it can at times be necessary to deviate from the amounts mentioned, and in particular to do so as a function of the body weight of the experimental animal or of the nature of the administration route, but also because of the species of animal and its individual behaviour towards the medicament, or the nature of the formulation of the medicament and the time or interval over which the administration takes place. Thus it can suffice in some cases to manage with less than the abovementioned minimum amount, whilst in other cases the upper limit mentioned must be exceeded. Where relatively large amounts are administered, it can be advisable to divide these into several individual administrations over the course of the day. The same dosage range is envisaged for administration in human medicine. In this connection, the above statements similarly apply.

PREPARATION EXAMPLES

Example 1

Ethyl 2-methyl-1-H-pyrido-[3,2-b][1,4]-thiazine-3-carboxylate

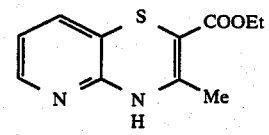

A solution or fine suspension of 5.0 g (23.1 mmol) of 2-amino-3-(benzylthio)-pyridine is prepared in 150 ml of liquefied ammonium under reflux, 2.0 g of sodium metal are added, and the mixture is stirred at −80° C. for about 45 minutes. Solid ammonium chloride is added until the reaction mixture decolorizes, and the ammonia is allowed to evaporate. After the residue has been dried under high vacuum, it is taken up in 100 ml of ethanol and, at about 10° C., 3.8 g (23.1 mmol) of ethyl 2-chloroacetoacetate are added with stirring. After about 15 minutes, the reaction mixture is made weakly acid by addition of 50% strength ethanolic acetic acid and is finally heated at 40°-50° C. until the reaction is complete.

After cooling, half of the solvent is removed by evaporation under water pump vacuum, 100 cm³ of ice water are added, and the reaction mixture is made weakly alkaline by addition of sodium bicarbonate and is extracted with ethyl acetate or dichloromethane. The combined organic extracts are dried over anhydrous sodium sulphate, the solvent is removed, and the residue is recrystallized or purified by column chromatography.

Yield: 64%.

Melting point: 104°-106° C.

The following are obtained in analogy to Example 1:

| Example | Structure | Yield (%) | Melting point (°C.) |
|---|---|---|---|
| 2 | pyrido-thiazine with =CH–CH₂COOEt substituent | 63 | 85–86 |
| 3 | 6-Me-pyrido-thiazine, NH, =C(Me)–C(=O)NHBuᵗ | 24 | 125–127 |
| 4 | pyrido-thiazine, NH, =C(Me)–C(=O)NMe₂ | 80 | 179–180 |
| 5 | pyrido-thiazine, NH, with two COOEt on C=C | 75 | 123–124 |
| 6 | pyrido-thiazine fused with cyclohexanone (NH) | 70 | 206–208 |
| 7 | 6-Cl-pyrido-thiazine fused with cyclohexanone (NH) | 20 | 218–223 |
| 8 | 6-morpholino-pyrido-thiazine, =CH–COOEt, NH | 80 | 168–169 |
| 9 | 6-EtO-pyrido-thiazine, =CH–COOEt, NH | 25 | 194–196 |
| 10 | 6-morpholino-pyrido-thiazine fused with cyclohexanone, NH | 74 | 220–222 |

-continued

| Example | | Yield (%) | Melting point (°C.) |
|---|---|---|---|
| 11 | (structure: pyrido-thiazine with C(=O)NH2 and Me) | 45 | 184–186 |
| 12 | (structure: EtO-pyrido-thiazine fused with cyclohexanone) | 51 | 208–210 |
| 13 | (structure: N-methylpiperazinyl-pyrido-thiazine with COOEt) | 59 | 252–253 |
| 14 | (structure: N-methylpiperazinyl-pyrido-thiazine fused with cyclohexanone) | 52 | 209–211 |

EXAMPLE 15

Methyl 7-methyl-1H-pyrido[3,2-b][1,4]-thiazine-3-carboxylate

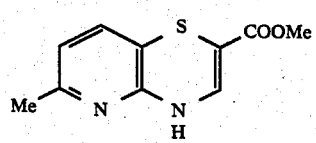

1.78 g (31.7 mmol) of potassium hydroxide are added under nitrogen to 4.44 g (31.7 mmol) of 2-amino-6-methyl-3-pyridinethiol in 200 ml of methanol, and the mixture is stirred at room temperature for about 30 minutes. Now, at 10° C., a solution of 4.8 g (35.2 mmol) of methyl 2-chloroformylacetate in 70 ml of methanol is added with stirring. The mixture is heated at 50° C. for 2 hours and worked up as described in Example 1.

Yield: 45%.
Melting point: 178°–180° C.

The following are obtained in analogy to Example 15:

| | | Yield | m.p. |
|---|---|---|---|
| (pyrido-thiazine with COOMe) | | 42 | 178–180 |
| (pyrido-thiazine with COOEt) | | 55 | 130–132 |
| (EtO-pyrido-thiazine with COOMe) | | 59 | 206–208 |
| (Me-pyrido-thiazine with COOEt and pentyl chain) | | 43 | 102 |
| (Me-pyrido-thiazine with two COOEt) | | 75 | 134–135 |
| (Me-pyrido-thiazine with COOEt and ethyl chain) | | 82 | 122–123 |

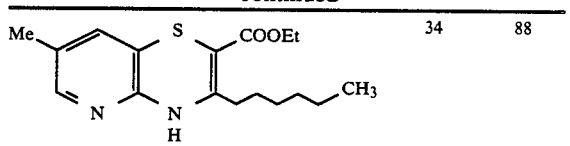

USE EXAMPLES

The lipoxygenase-inhibiting properties of the 1H-pyrido[3,2-b][1,4]thiazine of the general formula (I) are demonstrated in analogy to the methods of P. Borgeat and B. Samuelson, Proc. Nat. Acad. Sci. 76 2148-2152 (1979) and J. G. Hamilton and R. J. Karol, Progr. Lipid Res. 21 155-170 (1982).

Polymorphonuclear rat leukocytes were obtained from the peritoneal cavity of Wistar rats 18 hours after i.p. administration of 6 ml of a 12% strength sodium caseinate suspension.

The release of leukotriene $B_4$ on polymorphonuclear granulocytes after addition of substances and calcium ionophore was determined by HPLC as a measure of the inhibition of lipoxygenase.

After centrifugation and washing of the PMNL with incubation buffer (137 mM NaCl; 2.7 mM KCl; 5.0 mM $Na_2HPO_4$; 5.55 mM glucose; 2.0 mM $CaCl_2$ pH=7.2), the cell density was adjusted to $2 \times 10^7$ $ml^{-1}$ (Coulter Counter), and 1 ml of this cell suspension was preincubated with 2.5 μl of DMSO or 2.5 μl of various test substance concentrations in DMSO at 37° C. for 5 min. After stimulation of the cells with 2.5 μl of calcium ionophore A 23187 (1 mg $ml^{-1}$ in DMSO), the 6-minute main incubation was stopped by addition of 1.5 ml of $PGB_2$-containing methanol (1 μg $ml^{-1}$), and 2 ml of cell-free supernatant was obtained by centrifugation (1000 g, 3 min, RT) and, after acidification with 1N HCl to pH 3.0, was extracted twice with 4 ml of ether. The combined ether phases were washed with 4 ml of water (double-distilled) and dried under a stream of nitrogen, and the residue was taken up in 80 μl of methanol. 29 μl of each of the samples which had thus been prepared were loaded onto a prepacked column (Nucleosil, type 7.5 C 18; 4×25 mm) and chromatographed at a flow rate of 1 ml/min (Kontron 600 pump system), methanol, $H_2O$ and acetic acid (75:25:0.01) being used as mobile phase. Detection took place at 280 nm (Uvicon 720 LC). The formation of the metabolite was quantified by use of the internal standard protacylandin $B_2$ and inhibition was determined as a percentage of the controls.

As is evident from the table below, the 1H-pyrido[3,2-b][1,4]thiazines according to the invention, of the general formula (I), bring about significant inhibition of $LTB_4$ biosynthesis in rat granulocytes.

| Inhibition of leukotriene biosynthesis | |
|---|---|
| Compound from Example No. | g $ml^{-1}$ |
| 1 | 47% $2.4 \times 10^{-6}$ |
| 15 | 65% $2.2 \times 10^{-7}$ |
| 16 | 98% $2.1 \times 10^{-6}$ |
| 5 | 63% $2.9 \times 10^{-6}$ |

The antiasthmatic effect of the compounds according to the invention can likewise be demonstrated by methods which are already known (compare Samuelsson et al., FEBS Lett. 110 213 (1980) and Yen et al., Agents and Actions 10 274 (1980)).

What is claimed is:

1. A 1-H-pyrido[3,2-b][1,4]-thiazine of the formula

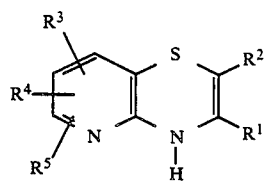

in which $R^1$ represents hydrogen, optionally substituted $C_1$ to $C_8$ alkyl or $C_2$ to $C_8$-alkenyl, or the group

in which $R^6$ represents optionally substituted $C_1$ to $C_8$ alkyl, $C_1$ to $C_8$ alkoxy or $C_6$ to $C_{12}$ aryl, $R^2$ represents hydrogen, nitrile, the group

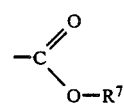

in which $R^7$ represents optionally substituted $C_1$ to $C_8$ alkyl, or the group

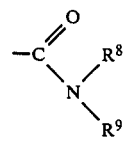

in which $R^8$ and $R^9$ each independently represent hydrogen, optionally substituted $C_1$ to $C_8$ alkyl or $C_6$ to $C_{12}$ aryl, and it being possible for the radicals $R^8$ and $R^9$ together with the nitrogen to which they are attached to form a 5- or 6-membered, optionally substituted heterocycle or additionally a pyrimidyl, imidazolyl, morpholinyl, thiomorpholinyl, piperazinyl or N-methyl piperazinyl, further $R^2$ represents the group

in which $R^{10}$ represents optionally substituted $C_1$ to $C_8$ alkyl, it being possible for $R^1$ and $R^{10}$ to form an optionally substituted 5- to 8-membered carbocycle, or optionally substituted $C_6$ to $C_{12}$ aryl, $R^3$ represents hydrogen, and $R^4$ and $R^5$ each independently represent hydrogen, halogen, optionally substituted $C_1$ to $C_8$ alkyl, $C_1$ to $C_8$ alkoxy, $C_6$ to $C_{12}$ aryloxy, $C_1$ to $C_8$ alkylthio, $C_6$ to $C_{12}$ arylthio or the group

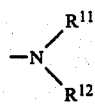

in which
R$^{11}$ and R$^{12}$ each independently represent hydrogen, optionally substituted C$_1$ to C$_8$ alkyl, or C$_6$ to C$_{12}$ aryl, and it being possible for the radicals R$^{11}$ and R$^{12}$ together with the nitrogen to which they are attached to form a 5- or 6-membered, optionally substituted heterocycle and additionally a pyrimidyl, imidazolyl, morpholinyl, thiomorpholinyl piperazinyl or N-methyl piperizinyl, and salts thereof wherein the optional substituents mentioned for the radicals hereinabove are halogen, nitro, cyano, methoxycarbonyl, ethoxycarbonyl, and trifluoromethyl.

2. A 1-H-pyrido-[3,2-b][1,4]-thiazine according to claim 1,
in which
R$^1$ represents hydrogen, C$_1$ to C$_6$ alkyl which is optionally substituted by carboxymethyl or carboxyethyl, or vinyl or carboxyethyl or carboxyethyl,
R$^2$ represents hydrogen, nitrile, carboxymethyl, carboxyethyl, or the group

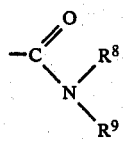

in which
R$^8$ and R$^9$ each independently represent hydrogen, C$_1$ to C$_6$ alkyl or phenyl and it being possible for the radicals R$^8$ and R$^9$ together with the nitrogen to which they are attached to be linked to form a piperidyl, morpholinyl, piperazinyl or N-methylpiperazinyl radical, further R$^2$ represents the group

in which
R$^{10}$ represents methyl or ethyl, and it being possible for R$^1$ and R$^{10}$ to form a 5- to 8-membered carbocycle which is optionally substituted by one or two methyl groups,
R$^3$ and R$^4$ represent hydrogen, C$_1$ to C$_6$ alkyl or halogen, and
R$^5$ represents hydrogen, fluorine, chlorine, bromine, C$_1$ to C$_6$ alkyl, C$_1$ to C$_6$ alkoxy, piperidyl, morpholinyl or N-methylpiperazinyl, and salts thereof.

3. A 1-H-pyrido[3,2-b][1,4]-thiazine according to claim 1 of the formula

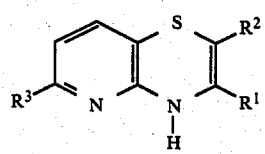

in which R$^1$, R$^2$ and R$^3$ are given by the following table

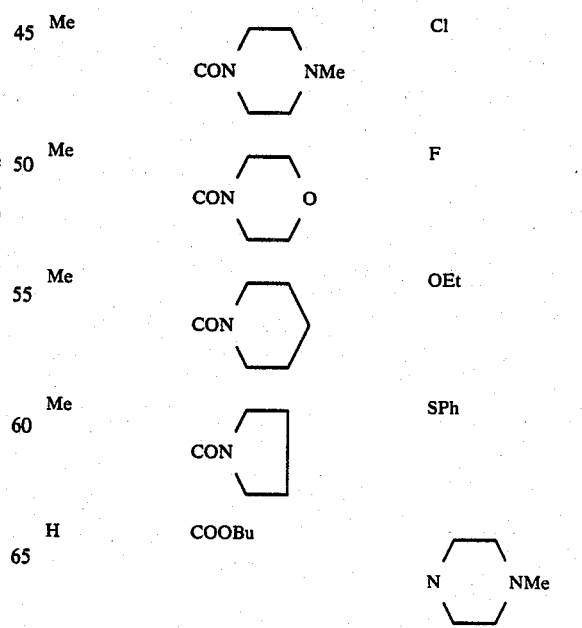

| R$^1$ | R$^2$ | R$^3$ |
|---|---|---|
| H | COOMe | Et |
| H | COOBu | Me |
| H | COOBu$^t$ | H |
| Me | COOMe | Et |
| Me | COOBu | Me |
| Me | COOBu$^t$ | H |
| Bu$^t$ | COOMe | Et |
| Bu$^t$ | COOBu | Me |
| Bu$^t$ | COOBu$^t$ | H |
| Me | COOEt | F |
| Me | COOPr$^i$ | Cl |
| Me | COOBu$^t$ | Br |
| H | CONH$_2$ | OEt |
| Me | CONHMe | O(p-Cl—Ph) |
| Et | CONHBu | O(o-CN—Ph) |
| Pr | CONPh | O(m-NO$_2$—Ph) |
| Pr$^i$ | CONHCH$_2$CH$_2$OH | SBu |
| Bu | CONHCH$_2$CH$_2$OMe | S(p-Cl—Ph) |
| Bu$^i$ | CONCH$_2$CH$_2$NH$_2$ | S(o-OMe—Ph) |
| Bu$^t$ | CONCH$_2$CH$_2$NHEt | S(m-NO$_2$—Ph) |
| H | CONHCH$_2$CH$_2$NMe$_2$ | NMe$_2$ |
| Me | CONMe$_2$ | NEt$_2$ |
| Et | CONMeEt | NMePh |
| Me | CN | Me |
| COOEt | COOEt | Me |
| COOBu | COOBu | Me |
| COOEt | H | H |
| CH$_2$COOEt | H | H |
| CH$_2$COOBu$^t$ | H | H |
| Me | COOEt | N(CH$_2$CH$_2$OMe)$_2$ |
| Me | COOEt | N(CH$_2$CH$_2$NMe$_2$)$_2$ |
| Et | COOCH$_2$CHF$_2$ | NEt(p-F—Ph) |
| Me | COOCH$_2$CH$_2$Cl | NMe(m-NO$_2$—Ph) |
| H | COOCH$_2$CN(Me)OMe | NMe(p-Me—Ph) |
| Bu$^t$ | COOCH$_2$CH$_2$CH$_2$OMe | NMe(p-Cl—Ph) |
| CH=CH$_2$ | H | H |
| H | Ph | H |
| H | p-Cl—Ph | H |
| H | p-OMe—Ph | H |
| H | m-CN—Ph | Me |
| H | m-NO$_2$—Ph | Cl |
| H | o-Br—Ph | Br |
| H | o-F—Ph | F |
| H | CO—Me | H |
| H | CO—Et | OEt |
| Me | CON(piperazinyl)NMe | Cl |
| Me | CON(morpholinyl) | F |
| Me | CON(piperidyl) | OEt |
| Me | CON(pyrrolidinyl) | SPh |
| H | COOBu | N(piperazinyl)NMe |

-continued

| R¹ | R² | R³ |
|---|---|---|
| H | COOBu | 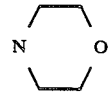 |
| H | CONEt₂ |  |
| H | CONEt₂ | 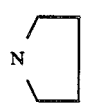 |
|  | | Me |
| 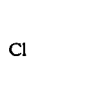 | | Cl |
| 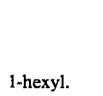 | | 1-hexyl. |

4. A 1-H-pyrido[3,2-b][1,4]-thiazine according to claim 1 of the formula

in which R¹, R² and R³ are given by the following table

| R¹ | R² | R³ | R⁴ |
|---|---|---|---|
| Me | COOEt | H | H |
| CH₂COOet | H | H | H |
| Me | CONHBuⁱ | Me | H |
| Me | CONMe₂ | H | H |
| COOet | COOEt | H | H |

-continued

| R¹ | R² | R³ | R⁴ |
|---|---|---|---|
| 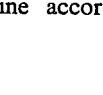 | H | H | H |
| 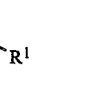 | Cl | H | H |
| H | COOEt | 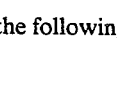 | H |
| H | COOEt | OEt | H |
|  | COOEt |  | H |
| Me | CONH₂ | H | H |
|  | | OEt | H |
| H | COOEt |  | H |
|  | |  | H |
| H | COOMe | Me | H |
| H | COOMe | H | H |
| H | COOEt | H | H |
| H | COOMe | OEt | H |
| 1-hexyl | COOEt | Me | H |
| COOEt | COOEt | H | Me |
| CH₂—CH₂—CH₃ | COOEt | H | Me |
| 1-hexyl | COOEt | H | Me. |

5. A 1-H-pyrido[3,2-b][1,4]-thiazine according to claim 1 selected from ethyl-2-methyl-1-H-pyrido-[3,2-b][1,4]-thiazine-3-carboxylate, ethyl-2-carboethoxy-1-H-pyrido-[3,2-b][1,4]-3-carboxylate, methyl-7-methyl-1-H-pyrido[3,2-b][1,4]-thiazine-3-carboxylate and methyl-1-H-pyrido[3,2-b][1,4]-thiazine-3-carboxylate.

6. A pharmaceutical composition comprising an effective amount of one or more 1-H-pyrido-[3,2-b][1,4]thiazines according to claim 1 and pharmaceutically suitable vehicle or solvent therefor.

7. A method of inhibiting lipoxygenase in a patient requiring such treatment comprising administering to said patient an effective amount of one or more 1-H-pyrido[3,2-b][1,4]-thiazines according to claim 1.

* * * * *

UNITED STATES PATENT AND TRADEMARK OFFICE
CERTIFICATE OF CORRECTION

PATENT NO. : 4,784,997

DATED : November 15, 1988

INVENTOR(S) : Alexander Klausener, et al

Page 1 of 2

It is certified that error appears in the above-identified patent and that said Letters Patent is hereby corrected as shown below:

| | |
|---|---|
| Col. 1, line 45 | Delete "$R_7$" and substitute --$R^7$-- |
| Col. 2, line 28 | Delete "b[1,4]" and substitute --b] [1,4]-- |
| Col. 2, line 37 | Correct spelling of --double-- |
| Col. 2, line 60 | Delete "en-lone" and substitute --en-1-one-- |
| Col. 6, line 5 | Correct --chlorine-- |
| Col. 11, line 21 | Delete "b] [1,49" and substitute --b] [1,4]-- |
| Col. 21, line 64 | Before formula insert --16-- |
| Col. 22, line 40 | Before formula insert --17-- |
| Col. 22, line 46 | Before formula insert --18-- |
| Col. 22, line 52 | Before formula insert --19-- |
| Col. 22, line 57 | Before formula insert --20-- |
| Col. 22, line 64 | Before formula insert --21-- |
| Col. 23, line 5 | Before formula insert --22-- |
| Col. 23, line 14 | Correct spelling of --Samuelsson-- |
| Col. 23, line 43 | Delete "29 µl" and substitute --20 µl-- |
| Col. 25, line 26 | After "vinyl or" delete "carboxyethyl" and substitute --carboxymethyl-- |

UNITED STATES PATENT AND TRADEMARK OFFICE
CERTIFICATE OF CORRECTION

PATENT NO. : 4,784,997

DATED : November 15, 1988

INVENTOR(S) : Alexander Klausener, et al.

It is certified that error appears in the above-identified patent and that said Letters Patent is hereby corrected as shown below:

Col. 28, line 62                  After "[1,4]" insert -- - --

Signed and Sealed this

Nineteenth Day of September, 1989

Attest:

DONALD J. QUIGG

*Attesting Officer*        *Commissioner of Patents and Trademarks*